United States Patent
Uyama et al.

(10) Patent No.: US 10,758,471 B2
(45) Date of Patent: Sep. 1, 2020

(54) COPOLYMER AND OILY GELLING AGENT

(71) Applicants: SHISEIDO COMPANY, LTD., Tokyo (JP); GOO CHEMICAL CO., LTD., Kyoto (JP)

(72) Inventors: Makoto Uyama, Yokohama (JP); Kazuyuki Miyazawa, Yokohama (JP); Takumi Watanabe, Yokohama (JP); Mineo Abe, Kyoto (JP); Masato Matsumura, Kyoto (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/536,027

(22) PCT Filed: Oct. 27, 2015

(86) PCT No.: PCT/JP2015/080236
§ 371 (c)(1),
(2) Date: Jun. 14, 2017

(87) PCT Pub. No.: WO2016/098456
PCT Pub. Date: Jun. 23, 2016

(65) Prior Publication Data
US 2017/0348219 A1    Dec. 7, 2017

(30) Foreign Application Priority Data
Dec. 19, 2014 (JP) ................. 2014-257488

(51) Int. Cl.
*C08F 220/58* (2006.01)
*C08F 220/54* (2006.01)
(Continued)

(52) U.S. Cl.
CPC ............ *A61K 8/8164* (2013.01); *A61K 8/042* (2013.01); *A61K 8/8152* (2013.01);
(Continued)

(58) Field of Classification Search
CPC ............................ C08F 220/12; C08F 220/18
See application file for complete search history.

(56) References Cited

U.S. PATENT DOCUMENTS

2001/0007881 A1* 7/2001 Bitler ..................... C08G 59/18
523/136

FOREIGN PATENT DOCUMENTS

| CN | 1387836 | 1/2003 |
|---|---|---|
| EP | 2 030 608 | 8/2000 |

(Continued)

OTHER PUBLICATIONS

Machine translation of JPS63309503. (Year: 1988).*
(Continued)

*Primary Examiner* — Wenwen Cai
(74) *Attorney, Agent, or Firm* — Andrew F. Young, Esq.; Lackenbach Siegel, LLP

(57) ABSTRACT

Copolymers derived from hydrophobic monomers of formula (1), and hydrophilic monomers of formulas (2) and (3), are provided

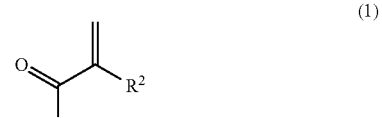

(1)

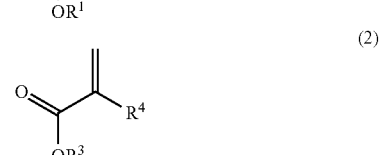

(2)

(Continued)

* Test example 1-2 G'
○ Test example 1-2 G"
* Dimethyl silylated silicic anhydride G'
* Dimethyl silylated silicic anhydride G"
▲ Dextrin palmitate G'
△ Dextrin palmitate G"
* Glyceryl (behenate/eicosanedioate) G'
○ Glyceryl (behenate/eicosanedioate) G"
◆ Microcrystalline wax G'
◇ Microcrystalline wax G"

-continued

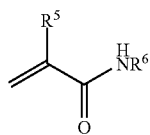

(3)

The copolymers are useful as gelling agents for oils used in cosmetics and cosmetic emulsions.

8 Claims, 4 Drawing Sheets

(51) Int. Cl.
*C08F 220/12* (2006.01)
*A61K 8/81* (2006.01)
*A61Q 1/00* (2006.01)
*A61Q 1/06* (2006.01)
*C08F 220/18* (2006.01)
*A61K 8/04* (2006.01)
*A61Q 1/10* (2006.01)
*A61Q 5/00* (2006.01)
*A61Q 19/00* (2006.01)
*A61Q 19/10* (2006.01)

(52) U.S. Cl.
CPC .............. *A61K 8/8158* (2013.01); *A61Q 1/00* (2013.01); *A61Q 1/06* (2013.01); *A61Q 1/10* (2013.01); *A61Q 5/00* (2013.01); *A61Q 19/00* (2013.01); *A61Q 19/10* (2013.01); *C08F 220/12* (2013.01); *C08F 220/18* (2013.01); *C08F 220/54* (2013.01); *C08F 220/58* (2013.01); *A61K 2800/10* (2013.01); *C08F 220/585* (2020.02)

(56) References Cited

FOREIGN PATENT DOCUMENTS

| | | |
|---|---|---|
| EP | 1 262 164 | 4/2002 |
| JP | 63-309503 | 12/1988 |
| JP | H05320562 A | * 12/1993 |
| JP | 11-326916 | 11/1999 |
| JP | 2003-509539 | 3/2003 |
| JP | 2003-238348 | 8/2003 |
| JP | 2008-133358 | 6/2008 |
| JP | 2011-079871 | 4/2011 |
| JP | 2012-233178 | 11/2012 |
| JP | 2015-131767 | 7/2015 |
| TW | 201429503 | 8/2014 |
| WO | WO 03/028766 | 4/2003 |

OTHER PUBLICATIONS

Machine translation of JPH05320562 A (Year: 1993).*
PCT/JP2015/080236, ISR and Written Opinion, dated Feb. 2, 2016, 8 pages—Japanese, 2 pages—English.
Ep 15869664.1, European Extended Search Report and Written Opinion dated Jun. 11, 2018, 6 pages—English.
TW104141899, Office Action dated May 29, 2019, 9 pages—Chinese; 8 pages—English.
JP 2016-564723, Office Action dated May 12, 2020, 2 pages—Japanese; 2 pages—English.

* cited by examiner

COPOLYMER AND OILY GELLING AGENT

RELATED APPLICATIONS

This application claims the priority of, Ser. No. PCT/JP2015/080236 filed Oct. 27, 2015, which is incorporated herein by reference, which in turn claims the priority of Japanese Patent Application No. 2014-257488 filed on Dec. 19, 2014, which is incorporated herein by reference.

FIELD OF THE INVENTION

The present invention relates to a novel copolymer, and in particular, relates to the copolymer to a form of a stable oily gelled composition, wherein the copolymer acts an oily gelling agent.

BACKGROUND OF THE INVENTION

Conventionally, gelled compositions have been used in various fields including such as cosmetics and foods, wherein an oily gelling agent is generally used to form such gelled composition containing oils.

For example, fats and oils contains at least 70% by mass of a triglyceride derived from a mixture of palmitic acid and behenic acid, wherein the mass ratio of each acid is 30:70 to 70:30, and the iodine value thereof is 10 or smaller, is used as the oily gelling agent (Patent Literature 1).

However, the stability of such oily gelled composition and particularly the temperature stability of the above oily gelled compositions are still needed to be further improved.

Patent Document

Patent literature 1: Japanese unexamined patent publication No. 2008-133358

DISCLOSURE OF THE INVENTION

Problem to be Solved by the Invention

The present invention is made in view of the above-described conventional art, and the problem to be solved is stability of oily gelled composition, and whether the new copolymer can improve such stabilities simply by just adjusting the proportion of respective monomers (to form the copolymer).

Means to Solve the Problem

The present inventor and associates diligently studying to solve the above-described stability problems found that a copolymer, comprising both a specific hydrophobic monomer and a specific hydrophilic monomer, achieves to provide an extremely stable oily gelled composition; and completed the present invention successfully.

Specifically, the copolymer of the present invention comprises a hydrophobic monomer having the following general (chemical) formula (1) and a hydrophilic monomer having the following general formula (2) or the following general formula (3).

[General formula (1)]

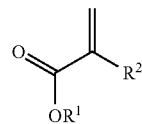

(1)

In the formula (1), $R^1$ is a straight-chained or branched alkyl group, having 16 to 22 carbon atoms. $R^2$ is a hydrogen atom or a methyl group.

[General formula (2)]

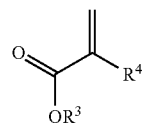

(2)

In the formula (2), $R^3$ is one selected from a group consisting of hydrogen atom, glyceryl group, a hydroxyalkyl group having straight-chained or branched carbon chain containing 1 to 4 carbon atoms, and polypropylene glycol group ($-(C_3H_6O)_nH$, in which n is an integer of 2 to 10). $R^4$ is a hydrogen atom or a methyl group.

[General formula (3)]

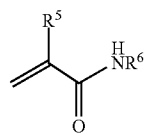

(3)

In the formula (3), $R^5$ is a hydrogen atom or a methyl group. $R^6$ is a straight-chained alkyl group; a branched alkyl group; a hydroxyalkyl group, in which each chain group has 1 to 4 carbon atoms; or a substituent having the following structural formula (4).

[Structural formula 4]

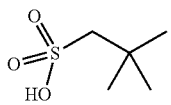

(4)

Relative to the above-described copolymer, it is preferable that the hydrophilic monomer represented by the general formula (1) is selected one from a group consisting of cetyl (meth)acrylate, stearyl (meth)acrylate, and behenyl (meth)acrylate.

Relative to the above-described copolymer, it is preferable that the hydrophilic monomer represented by the general formula (3) is selected one from a group consisting of N-(2-hydroxyethyl)acrylamide, N-isopropylacrylamide, and 2-acrylamido-2-methylpropanesulfonic acid.

Relative to the above-described copolymer, it is preferable that the hydrophilic monomer represented by the general formula (2) is selected one from a group consisting of 2-hydroxyethyl acrylate, glyceryl methacrylate, 2-hydroxyethyl methacrylate, PPG-6 acrylate, 2-hydroxypropyl methacrylate, 2-hydroxy-2-methylpropyl methacrylate, and acrylic acid.

Relative to the above-described copolymer, it is preferable that a total of the hydrophobic monomer represented by the general formula (1) and one hydrophilic monomer represented by either the general formula (2) or the general formula (3) is at least 90% of the total monomers.

Relative to the above-described copolymer, it is preferable that the mole ratio between the hydrophobic monomer and the hydrophilic monomer is 3:7 to 8:2 (mole ratio).

Relative to the above-described copolymer, it is preferable that the hydrophilic monomer represented by the general formula (2) or the general formula (3) is one selected from a group consisting of N-(2-hydroxyethyl)acrylamide, 2-hydroxyethyl acrylate, and glyceryl methacrylate.

The copolymer of the present invention is formed from a hydrophobic monomer represented by the general formula (1) set forth above and at least one hydrophilic monomer represented by either general formula (2) or the general formula (3) set forth above.

The oily gelling agent of the present invention is the above-described copolymer.

The oily gelled composition of the present invention is formed from the above-described oily gelling agent.

The oily cosmetic of the present invention comprises the above-described oily gelled composition.

The oily water-in-oil cosmetic of the present invention comprises the above-described oily gelled composition.

Effect of the Invention

According to the present invention, a novel copolymer is provided. In addition, an oily gelling agent to form a stable oily gelled composition is obtained simply by just adjusting the proportion of a hydrophobic monomer and a hydrophilic monomer therefor.

BEST MODE FOR CARRYING OUT THE INVENTION

Figure 1:
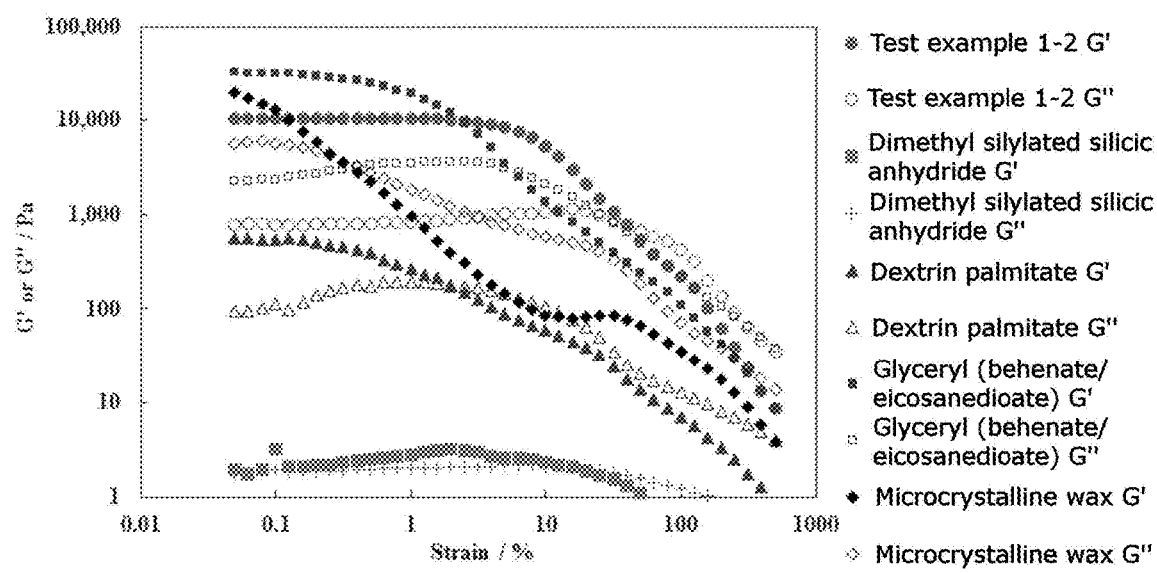
FIG. 1 is a graph that shows rheological measurement data (in which the oil is cetyl 2-ethylhexanoate).

The copolymer of the present invention is formed from a specific hydrophobic monomer and a specific hydrophilic monomer. Hereinafter, the respective monomers that form the copolymer are set forth in detail.

The hydrophobic monomer is at least one monomer represented by the following general formula (1).

[General formula (1)]

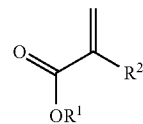

(1)

In the formula (1), $R^1$ is a straight chained or branched alkyl group, each having 16 to 22 carbon atoms.

Examples of straight chained alkyl group, having 16 to 22 carbon atoms, include a cetyl group, a stearyl group, an oleyl group, and a behenyl group; and an example of branched alkyl group, having 16 to 22 carbon atoms, includes an isostearyl group.

In the formula (1), $R^2$ is a hydrogen atom or a methyl group.

Such hydrophobic monomer is a (meth)acrylic acid alkyl ester (C16 to C22), namely the ester is derived from an acrylic acid or a methacrylic acid and an alcohol having a hydrocarbon group of 16 to 22 carbon atoms.

Specifically, examples of such esters include cetyl acrylate, cetyl methacrylate, stearyl acrylate, stearyl methacrylate, isostearyl acrylate, isostearyl methacrylate, oleyl acrylate, oleyl methacrylate, behenyl acrylate, and behenyl methacrylate.

The hydrophilic monomer being applied is at least one monomer represented by either following general formula (2) or general formula (3).

[General formula (2)]

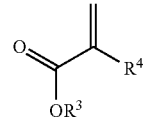

(2)

In the formula (2), $R^3$ is a hydrogen atom, a glyceryl group, a straight chained or branched hydroxyalkyl group having 1 to 4 carbon atoms, or a polypropylene glycol group ($-(C_3H_6O)_nH$).

Examples of such hydroxylalkyl groups include 2-hydroxyethyl group, 2-hydroxypropyl group, 2-hydroxyethyl-2-hydroxypropyl group, 2-hydroxybutyl group, 3-hydroxybutyl group, and 4-hydroxybutyl group.

Furthermore, "n" which represents the addition mole number of polypropylene glycol is an integer of 2 to 10.

In formula (2), $R^4$ is a hydrogen atom or a methyl group.

As the hydrophilic monomer represented by the following general formula (3), it is preferable to select one specifically from a group consisting of 2-hydroxyethyl acrylate (HEA), glyceryl methacrylate (GLM), 2-hydroxyethyl methacrylate (HEMA), PPG-6 acrylate (AP-400), 2-hydroxypropyl methacrylate (HPMA), 2-hydroxy-2-methylpropyl methacrylate (HBMA), and acrylic acid (Aa).

[General formula (3)]

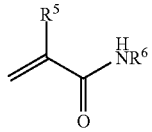

(3)

In the formula (3), $R^5$ is a hydrogen atom or a methyl group.

$R^6$ is a straight chained, a branched alkyl group or a hydroxyalkyl group, each having 1 to 4 carbon atoms; or a substituent represented by the following structural formula (4).

[Structural formula 4]

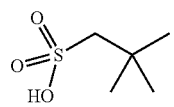

(4)

Examples of alkyl groups in $R^6$ include ethyl group, propyl group, isopropyl group, and butyl group.

Examples of hydroxylalkyl groups include 2-hydroxyethyl group, 2-hydroxypropyl group, 2-hydroxyethyl-2-hydroxypropyl group, 2-hydroxybutyl group, 3-hydroxybutyl group, and 4-hydroxybutyl group.

A hydrophilic monomer represented by the general formula (3) is preferably one selected specifically from a group consisting of N-(2-hydroxyethyl)acrylamide (HEAA), N-isopropylacrylamide (NIPAM), and 2-acrylamido-2-methylpropanesulfonic acid (AMPS).

A copolymer of the present invention is either a random-type copolymer or a block-type copolymer and a random-type copolymer is further preferable because the random copolymer is more easily synthesized than the block copolymer.

The copolymer of the present invention can be produced by the following method.

Specifically, a mixture of a hydrophobic monomer represented by the general formula (1), a hydrophilic monomer represented by the general formula (2) or general formula (3), and ethanol are introduced into a four-neck flask equipped with a reflux condenser, a thermometer, a nitrogen gas introducing tube, and a stirrer (a mixing device), and heated under nitrogen atmosphere. A polymerization initiator is added when reflux begins, and the mixture are refluxed for several hours to carry out a polymerization reaction. Subsequently, ethanol is added again to obtain the copolymer after the solvent in the solution is evaporated.

Examples of polymerization initiators include 2,2'-azobisisobutyronitrile. The reflux is preferably maintained for about 3 to 5 hours after the addition of the polymerization initiator.

The copolymer of the present invention is used as an oily gelling agent. A stable oily gelled composition is obtained by mixing the copolymer of the present invention.

In the copolymer of the present invention, a hydrophobic monomer represented by general formula (1) and a hydrophilic monomer represented by general formula (2) or general formula (3) are preferably at least 90% and more preferably 100% of the total monomers. If the hydrophobic monomer and hydrophilic monomer are less than 90%, such copolymer cannot act as an oily gelling agent.

Examples of hydrophobic monomers allowed to be contained in the copolymer of the present invention other than hydrophobic monomers represented by general formula (1) include methyl styrene, styrene, benzyl acrylate, benzyl methacrylate, phenyl acrylate, phenyl methacrylate, tris(trimethylsiloxy) silyl propyl methacrylate, 2-perfluorohexyl-2-ethyl acrylate, and 2-perfluorohexyl-2-ethyl methacrylate.

Examples of hydrophilic monomers allowed to be contained in the copolymer of the present invention other than hydrophilic monomers represented by general formula (2) or general formula (3) include vinylpyrrolidone, vinylimidazole, methoxypolyethylene glycol acrylate, methoxypolyethylene glycol methacrylate, N,N-dimethylacrylamide, N,N-diethylacrylamide, acroylmorpholine, N-(2-methacryloyloxyethyl)ethylene urea, and 2-methacryloyloxyethyl phosphorylcholine.

In the copolymer of the present invention, it is preferable that proportion of hydrophobic monomer to hydrophilic monomer, namely hydrophobic monomer vs hydrophilic monomer is preferably 3:7 to 8:2 (mole ratio) and more preferably 4:6 to 7:3 (mole ratio). If the percentage of the hydrophilic monomer is too high, it may not work as an oily gelling agent. If the percentage of the hydrophobic monomer is too high, the copolymer becomes opaque when used as an oily gelling agent, and the gel likely becomes a solid.

Relative to a hydrophobic monomer represented by general formula (1), cetyl acrylate, stearyl acrylate, and behenyl acrylate are preferably used. The copolymers derived from such hydrophobic monomers are excellent for the gelling property and extremely compatible with oil when the copolymers are used as an oily gelling agent.

Relative to a hydrophilic monomer represented by general formula (2) or general formula (3), N-(2-hydroxyethyl)acrylamide (HEAA), 2-hydroxyethyl acrylate (HEA), and glyceryl methacrylate (GLM) is preferably used. The copolymers containing these hydrophilic monomers are excellent for the gelling property and extremely compatible with oil when the copolymers are used as an oily gelling agent.

If the copolymer of the present invention is used as oily gelling agent, the compatibility thereof with silicone oil is poor, and therefore it is difficult to achieve gelation. Thus, a hydrocarbon oil, an ester oil, and an alcohol as an oil component is preferably included in the oily gelation.

The sum of such hydrocarbon oil, ester oil, and alcohol is preferably 80% by mass or higher in the total oils, and more preferably 85% by mass or higher.

Examples of the hydrocarbon oils set forth above include liquid paraffin, tetraisobutane, hydrogenated polydecene, olefin oligomer, isododecane, isohexadecane, squalane, and hydrogenated polyisobutene.

Examples of the ester oils set forth above include cetyl 2-ethylhexanoate, triethylhexanoine, 2-ethylhexyl palmitate, neopentyl glycol dicaprate, triisostearin, diisostearyl malate, PPG-3 dipivalate, di2-ethylhexyl succinate, 2-ethylhexyl 2-ethylhexanoate, polyglyceryl-6 octacaprylate, and glyceryl tri(caprylate/caprate).

Examples of the alcohol set forth above include isostearyl alcohol and oleyl alcohol.

When an oily gelled composition is prepared, the preparation is easily performed when the copolymer of the present invention is dissolved in such hydrocarbon oil, ester oil and alcohol, respectively and then the copolymer therein is subject to be mixed with other components. The copolymer can be heated, if needed, during dissolution and mixing.

When the copolymer of the present invention is used as an oily gelling agent, the blending quantity is preferably 2% by mass or higher in the oily gelled composition, and more preferably 3% by mass or higher. If the blending quantity is 2% by mass or less, gelling may become poor. On the other hand, the blending quantity is preferably 10% by mass or less in the oily gelled composition, and more preferably 8% by mass or less. If the blending quantity exceeds 10% by mass, the compatibility thereof with oil may become poor.

The oily gelling agent of the present invention can achieve gelation with a small amount thereof, so that no stickiness due to the gelling agent takes place, and accordingly an oily gelled composition can suitably be obtained. Such oily gelled composition can suitably be blended into oil-based cosmetics and water-in-oil type emulsion cosmetics. If a solid or semi-solid oil at ordinary temperature, such as waxes, is used to solidify the oil, stickiness may be caused; however, when the oily gelled composition of the present invention is blended, stickiness is not generated.

Examples of oily cosmetics include oily gelled cosmetics such as skincare cosmetic (for example, beauty serum and etc.), make-up cosmetic (for example, lipstick, gross, and etc.), skin washing agent (for example, make-up remover and etc.), and hair cosmetic (for example, hair treatment and etc.) and oily cosmetics such as make-up cosmetic (for example, mascara, pre-mascara, and etc.), skin washing agent (for example, make-up remover and etc.), hair cosmetic (for example, hair oil and etc.), and sun-care oil.

Examples of water-in-oil cosmetics include skincare cosmetic (for example, lotion, milky lotion, cream, beauty serum, and etc.), make-up cosmetic (for example, foundation, pre-makeup, lipstick, blusher, eye shadow, mascara, pre-mascara, and etc.), skin washing agent (for example, body soap, facial wash, make-up remover, and etc.), hair washing agent (for example, shampoo and etc.), hair cosmetic (for example, rinse, hair treatment, hair growing agent, and etc.), sun-care cosmetic, and hair color.

In the oil-based cosmetics or water-in-oil type emulsion cosmetics, in which the oily gelled composition of the present invention is blended, components normally used in cosmetics, such as moisturizers, UV absorbers, perfumes, antioxidants, preservatives/fungicides, extender pigments, coloring pigments, and water can be blended.

EXAMPLES

The present invention is further described in the following examples. However, the invention is not limited to the below examples. Unless otherwise specified, the blending quantity of each component is expressed in % by mass.

Prior to illustrating the examples, the methods for the evaluation tests used in the present invention is explained.

Evaluation (1): Compatibility with Oil

The compatibility with oil is visually observed when a copolymer is dissolved in various oils at 85° C.
A: Compatible
B: Slight precipitation is observed.
C: Not compatible at all.

Evaluation (2): Gelling Capability

After 5% of a copolymer was dissolved in various oils at 85° C., it is cooled to 35° C. under stirring and then the state is observed. The state without fluidity in the tilt method is determined as a gel.
A: Gelation takes place.
B: Slight gelation takes place.
C: No gelation takes place.

Evaluation (3): Transparency
The transparency of a sample is visually evaluated.

Evaluation (4): Viscosity
A sample stored at room temperature (25° C.) for 1 hour right after production is measured with a B-type viscometer (BL model, 12 rpm).

Evaluation (5): Emulsion Particle Size
The average particle size of emulsion particles after sample preparation is evaluated by microscopic observation.

At first, the production method of the copolymer of the present invention is shown below.

A mixture of a hydrophobic monomer and a hydrophilic monomer in a proportion (mole ratio) shown in each test example (100 parts in total by mass), and 250 parts by mass of ethanol are poured into a 1L four-neck flask equipped with a reflux condenser, a thermometer, a nitrogen gas introducing tube, and a stirrer, and the mixture is heated under nitrogen atmosphere. When a reflux begins (at about 80° C.), 1 percent by mass of 2,2'-azobisisobutyronitrile is added, and the mixture is further refluxed for 4 hours to accomplish a polymerization reaction. Subsequently, the solvent is evaporated from the solution, and then ethanol is added to obtain the copolymer (as resin solution), in which the concentration of the copolymer is 50% by mass as a solid.

The present inventors investigated the gelling property of copolymers. Specifically, the copolymers, for which each hydrophobic monomer and hydrophilic monomer in the following Table 1 is used, were produced by the above-described production method, and evaluated by the above-described evaluation methods (1) and (2). Cetyl 2-ethylhexanoate was used as oil. The results are shown in Table 1.

In the following tables, the blending ratios of a hydrophobic monomer and a hydrophilic monomer are expressed in mole ratios.

In the following tables, hydrophobic monomers and hydrophilic monomers are shown in abbreviations.

The following abbreviations stand for each hydrophobic monomer in the below tables.
SA: stearyl acrylate (monomer represented by the general formula (1), $R^1$=stearyl group, $R^2$=hydrogen)
BEA: behenyl acrylate (monomer represented by the general formula (1), $R^1$=behenyl group, $R^2$=hydrogen)
2EHA: 2-ethylhexyl acrylate (monomer represented by the general formula (1), $R^1$=2-ethylhexyl group, $R^2$=hydrogen)
LA: lauryl acrylate (monomer represented by the general formula (1), $R^1$=lauryl group, $R^2$=hydrogen)
CA: cetyl acrylate (monomer represented by the general formula (1), $R^1$=cetyl group, $R^2$=hydrogen)

The official compound names of hydrophilic monomers in the tables are as follows.
HEAA: N-(2-hydroxyethyl)acrylamide (monomer represented by the general formula (3), $R^5$=hydrogen, $R^6$=hydroxyethyl group)
Aa: acrylic acid (monomer represented by the general formula (2), $R^3$=hydrogen, $R^4$=hydrogen)
AMPS: 2-acrylamido-2-methylpropanesulfonic acid (monomer represented by the general formula (3), $R^5$=hydrogen, $R^6$=substituent represented by the structural formula (4))
DAAM: diacetone acrylamide (monomer represented by the following structural formula (5))
NIPAM: N-isopropylacrylamide (monomer represented by the general formula (3), $R^5$=hydrogen, $R^6$=2-isopropyl group)
HEMA: 2-hydroxyethyl methacrylate (monomer represented by the general formula (2), $R^3$=2-hydroxyethyl group, $R^4$=methyl group)
HEA: 2-hydroxyethyl acrylate (monomer represented by the general formula (2), $R^3$=2-hydroxyethyl group, $R^4$=hydrogen)
GLM: glyceryl methacrylate (monomer represented by the general formula (2), $R^3$=glyceryl group, $R^4$=methyl group)
QA: N,N,N-trimethyl-N-(2-hydroxy-3-methacryloyloxypropyl)-ammonium chloride (monomer represented by the following structural formula (6))
AE-400: PEG-10 acrylate (monomer represented by the following structural formula (7)) AP-400: PPG-6 acrylate (monomer represented by the general formula (2), $R^3$=—$(C_3H_6O)_n$H (n=6), $R^4$=hydrogen)
HPMA: 2-hydroxypropyl methacrylate (monomer represented by the general formula (2), $R^3$=2-hydroxypropyl group, $R^4$=methyl group)

HBMA: 2-hydroxy-2-methylpropyl methacrylate (monomer represented by the general formula (2), $R^3$=2-hydroxy-2-methylpropyl group, $R^4$=methyl group)

[Structural formula (5)]

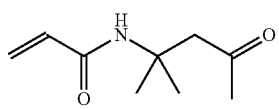

(5)

[Structural formula (6)]

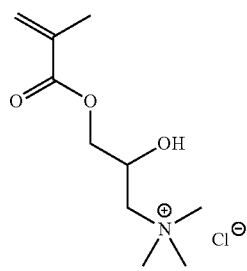

(6)

[Structural formula (7)]

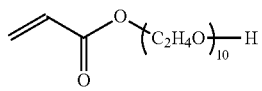

(7)

TABLE 1

| Test example | 1-1 | 1-2 |
|---|---|---|
| Hydrophobic monomer | SA | BEA |
|  | 50 | 60 |
| Hydrophilic monomer | HEAA | HEAA |
|  | 50 | 40 |
| Weight-average molecular weight (Mw) | 31,900 | — |
| Evaluation (1): Compatibility with oil | A | A |
| Evaluation (2): Gelling property | A | A |
| Evaluation (3): Transparency | translucence | translucence |

According to Table 1, the copolymer consisting of stearyl acrylate and N-(2-hydroxyethyl)acrylamide (Test Example 1-1) had a significant gelling capability when 5% of it was blended.

Furthermore, the copolymer consisting of behenyl acrylate and N-(2-hydroxyethyl)acrylamide (Test Example 1-2) also had a significant gelling capability when 5% of it was blended.

Therefore, the present inventors investigated the properties of the oily gel containing the copolymer of Test Example 1-2.

That is, the evaluation was carried out for an oily gel containing 5% of the copolymer of Test Example 1-2 or a publicly known oily gelling agent (dimethylsilyl silicic anhydride, dextrin palmitate, glyceryl behenate/eicosadioate, or microcrystalline wax) by the above-described evaluation methods (1) and (2). Cetyl 2-ethylhexanoate or olefin oligomer 30 was used as oil. The results are shown in Table 2.

As the publicly known oily gelling agents, the following products were used for investigation.

Dimethyl silylated silicic anhydride: AEROSIL R972 (manufactured from NIPPON AEROSIL CO., LTD.)

Dextrin palmitate: Rheopearl KL (manufactured from Chiba Flour Milling Co., Ltd.) Glyceryl (behenate/eicosadioate): NOMCORT HK-G (manufactured from The Nisshin OilliO Group, Ltd.)

Microcrystalline wax: PARMIC 160 (manufactured from NIKKO RICA CORPORATION)

In addition, after the evaluation by the above-described evaluation method (2), the rheological measurement of each sample was also carried out. That is, the storage modulus G' and loss modulus G" were measured with a cone/plate-type viscoelasticity measuring instrument MCR302 (manufactured by Anton Paar Germany GmbH) by using a plate PP25 (radius: 0.5 mm) as the measuring tool. The measurement conditions were $\gamma$=0.05 to 500% and f=1 Hz, and the measurement temperature was 20° C.

Figure 2:
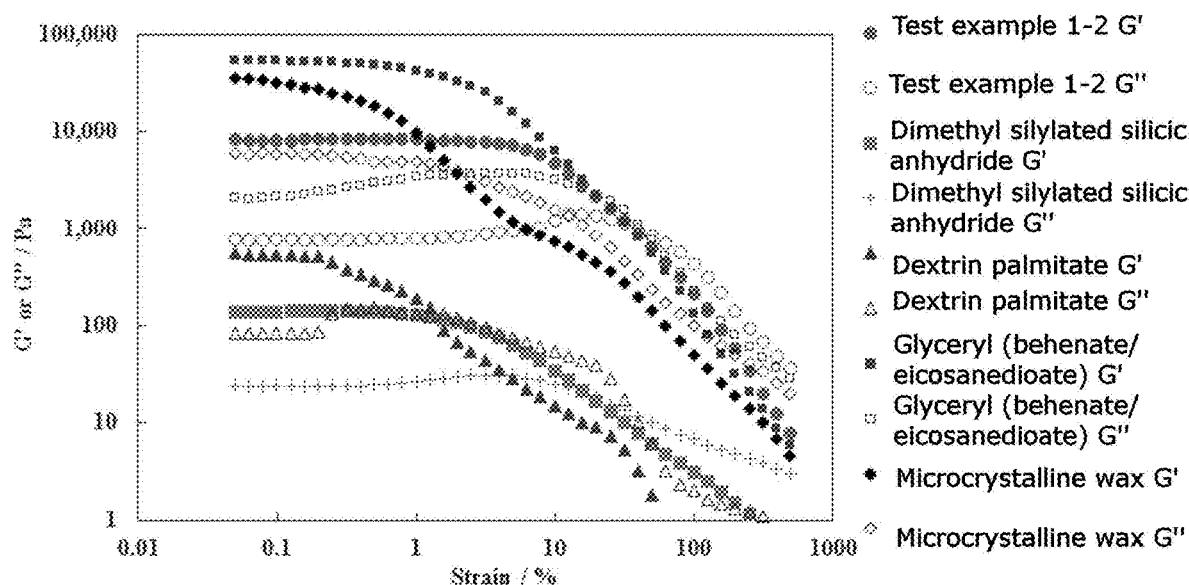
FIG. 2 is a graph that shows rheological measurement data (in which the oil is hydrogenated polydecene).

As the oil, hydrogenated polydecene as well as cetyl 2-ethylhexanoate was used in the measurement. The results are shown in FIG. 1 and FIG. 2, respectively.

In addition, the rheological measurement was carried out by varying the temperature for the sample of Test Example 1-2, glyceryl behenate/eicosadioate, and microcrystalline wax. The measurement equipment was the above-described instrument, the measurement conditions were $\gamma$=1% and f=1 Hz, and the measurement temperature was 0 to 60° C.

Figure 3:
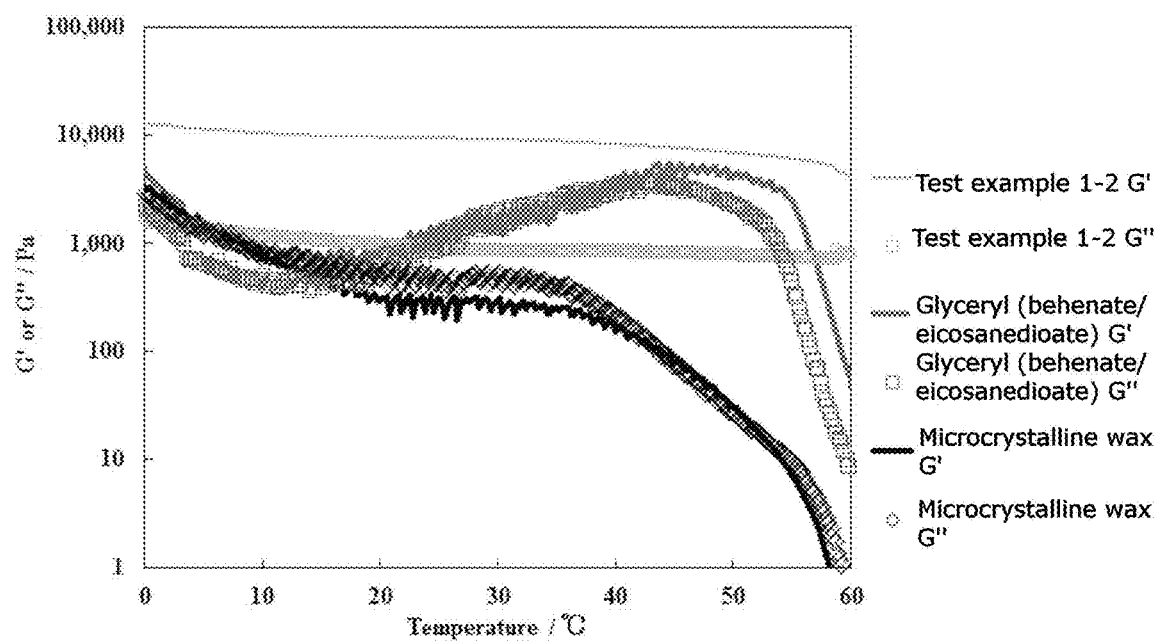
FIG. 3 is a graph that shows rheological measurement data (at a variety of temperatures) (wherein the oil is cetyl 2-ethylhexanoate).
Figure 4:
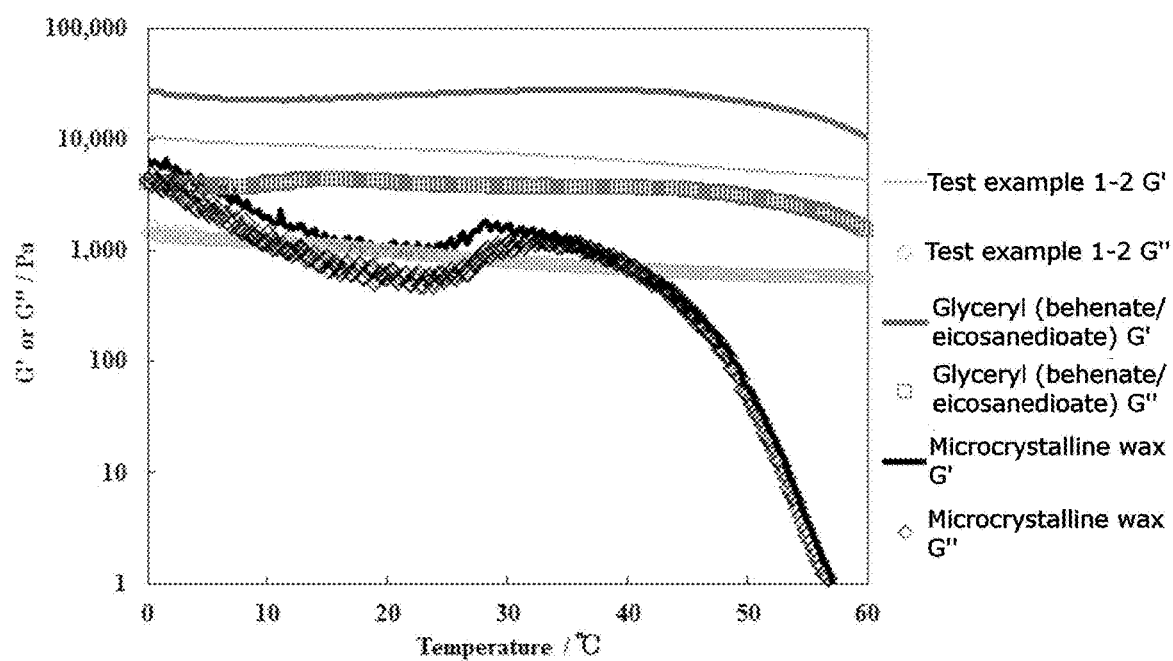
FIG. 4 is a graph that shows rheological measurement data (varying at a variety of temperatures) (in which the oil is hydrogenated polydecene).

Measurement took place by using cetyl 2-ethylhexanoate or hydrogenated polydecene as oil. The results are shown in FIG. 3 and FIG. 4, respectively.

TABLE 2

|  |  | Test example 1-2 | Dimethyl silylated silicic anhydride | Dextrin palmitate | Glyceryl (behenate/ eicosanedioate) | Microcrystalline wax |
|---|---|---|---|---|---|---|
| Evaluation (1): Compatibility with oil | Cetyl 2-ethylhexanoate | A | A | A | A | A |
| Evaluation (2): Gelling capability |  | A | C | A | A | A |
| Evaluation (1): Compatibility with oil | Olefin oligomer 30 | A | A | A | A | A |
| Evaluation (2): Gelling capability |  | A | C | C | A | A |

According to Table 2, all the oily gelling agents were soluble in cetyl 2-ethylhexanoate and olefin oligomer at 85° C.; however, some of them did not gelate depending upon combinations.

A sample of Test Example 1-2, glyceryl behenate/eicosadioate, and microcrystalline wax could form a gel with any oil.

According to FIG. 1 and FIG. 2, the samples of Test Example 1-2 were the strongest against strain, and there was a distinct linear region.

On the other hand, other samples had high G' on the lower strain side; however, they were weak against strain, and a linear region was hardly present.

According to FIG. 3 and FIG. 4, the samples of Test Example 1-2 were stable up to near 60° C. for both oils.

When cetyl 2-ethylhexanoate was used, glyceryl behenate/eicosadioate, and microcrystalline wax were in the breakdown region, and they were unstable regardless of temperature.

When hydrogenated polydecene was used, microcrystalline wax was in the breakdown region, and it was unstable regardless of temperature.

Thus, the oily gelled composition obtained from the copolymer of the present invention was the best in the strain and temperature stability.

Next, the kinds of hydrophobic monomers constituting the copolymer were investigated. That is, the copolymers, in which a hydrophobic monomer and a hydrophilic monomer shown in the following Table 3 were used, were produced by the above-described production method, and they were evaluated by the above-described evaluation methods (1) and (2). Cetyl 2-ethylhexanoate was used as oil. The results are shown in Table 3.

TABLE 3

| Test example | 2-1 | 2-2 | 2-3 | 2-4 | 1-2 |
|---|---|---|---|---|---|
| Hydrophobic monomer | 2EHA 50 | LA 60 | CA 60 | SA 60 | BEA 60 |
| Hydrophilic monomer | HEAA 50 | HEAA 40 | HEAA 40 | HEAA 40 | HEAA 40 |
| Weight-average molecular weight (Mw) | 31,400 | 31,100 | 16,200 | 15,300 | — |
| Evaluation (1): Compatibility with oil | B | B | A | A | A |
| Evaluation (2): Gelling capability | C | C | A | A | A |

According to Table 3, it is seen that when a (meth)acrylic acid alkyl ester (C8 to C12) is used as the hydrophobic monomer (Test Examples 2-1 and 2-2), they do not function as an oily gelling agent.

On the other hand, a copolymer in which a (meth)acrylic acid alkyl ester (C16 to C22) was used as the hydrophobic monomer was an excellent oily gelling agent.

Next, the kinds of hydrophilic monomers constituting the copolymer were investigated. That is, the copolymers, in which a hydrophobic monomer and a hydrophilic monomer shown in the following Tables 4 and 5 were used, were produced by the above-described production method, and they were evaluated by the above-described evaluation methods (1) and (2). Cetyl 2-ethylhexanoate was used as oil. The results are shown in Tables 4 and 5.

TABLE 4

| Test example | 3-1 | 3-2 | 3-3 | 3-4 | 3-5 | 3-6 | 3-7 | 3-8 |
|---|---|---|---|---|---|---|---|---|
| Hydrophobic monomer | SA 35 | SA 50 | SA 40 | SA 50 | SA 60 | SA 40 | SA 50 | SA 60 |
| Hydrophilic monomer | Aa 65 | AMPS 50 | DAAM 60 | DAAM 50 | DAAM 40 | NIPAM 60 | NIPAM 50 | NIPAM 40 |
| Weight-average molecular weight (Mw) | 36,700 | — | 36,300 | 16,400 | 21,100 | 34,600 | 37,700 | 29,700 |
| Evaluation (1): Compatibility with oil | B | B | A | A | A | A | A | A |
| Evaluation (2): Gelling capability | A | A | C | C | C | A | B | B |

TABLE 5

| Test example | 4-1 | 4-2 | 4-3 | 4-4 | 4-5 | 4-6 | 4-7 | 4-8 |
|---|---|---|---|---|---|---|---|---|
| Hydrophobic monomer | BEA 60 | BEA 60 | BEA 60 | BEA 60 | BEA 60 | BEA 60 | BEA 60 | BEA 60 |
| Hydrophilic monomer | HEMA 40 | HEA 40 | GLM 40 | QA 40 | AE-400 40 | AP-400 40 | HPMA 40 | HBMA 40 |
| Weight-average molecular weight (Mw) | 50,100 | 16,200 | 29,300 | — | — | 29,200 | 53,200 | 56,700 |
| Evaluation (1): Compatibility with oil | A | A | A | C | B | A | A | A |
| Evaluation (2): Gelling capability | B | A | A | C | C | B | B | B |

According to Table 4 and Table 5, it is seen that even when a (meth)acrylic acid alkyl ester (C16 to C22) is used as the hydrophobic monomer that constitutes a copolymer, some of them do not function as an oily gelling agent depending upon the kinds of hydrophilic monomers.

Thus, the copolymer of the present invention needs to contain a hydrophobic monomer hydrophobic monomer that is represented by general formula (1) and a hydrophilic monomer represented by general formula (2) or general formula (3).

Such a copolymer of the present invention is an oily gelling agent, with which a stable oily gelled composition can be prepared, and the compatibility with oil is also good. Furthermore, when the compatibility with oil and gelling capability are considered, it is preferable to use N-(2-hydroxyethyl)acrylamide (HEAA), 2-hydroxyethyl acrylate (HEA), or glyceryl methacrylate (GLM) as the hydrophilic monomer.

Next, the proportion (mole ratio) of a hydrophobic monomer and a hydrophilic monomer that form a copolymer was investigated. That is, the copolymers, in which a hydrophobic monomer and a hydrophilic monomer shown in the following Table 6 were used, were produced by the above-described production method, and they were evaluated by the above-described evaluation methods (1) to (3). Cetyl 2-ethylhexanoate was used as oil. In addition, HLBs of the copolymers were calculated. The results are shown in Table 6.

TABLE 6

| Test example | 5-1 | 2-4 | 5-2 | 5-3 | 5-4 | 5-5 | 5-6 | 5-7 |
|---|---|---|---|---|---|---|---|---|
| Hydrophobic monomer | SA 40 | SA 60 | BEA 20 | BEA 30 | BEA 40 | BEA 50 | BEA 70 | BEA 80 |
| Hydrophilic monomer | HEAA 60 | HEAA 40 | HEAA 80 | HEAA 70 | HEAA 60 | HEAA 50 | HEAA 30 | HEAA 20 |
| Hydrophobic monomer:Hydrophilic monomer | 4:6 | 6:4 | 2:8 | 3:7 | 4:6 | 5:5 | 7:3 | 8:2 |
| HLB | 8.9 | 5.3 | 14.0 | 10.4 | 7.8 | 6.0 | 3.5 | 2.6 |
| Evaluation (1): Compatibility with oil | A | A | C | A | A | A | A | A |
| Evaluation (2): Gelling capability | A | A | C | B | A | A | A | A |
| Evaluation (3): Transparency | translucence | translucence | — | transparence | translucence | translucence | translucence | translucence~opacity |

According to Table 6, when the proportion of the hydrophilic monomer (and HLB of the copolymer) was very high, gelation did not take place.

Furthermore, when the proportion of the hydrophobic monomer was very high, it became opaque. In addition, the gel properties became solid.

Accordingly, when the copolymer of the present invention is used as an oily gelling agent, the proportion of a hydrophobic monomer and a hydrophilic monomer, namely hydrophobic monomer vs hydrophilic monomer is preferably 3:7 to 8:2 (mole ratio). In addition, HLB of the copolymer is preferably 2 to 10.

Next, the blending quantity of a copolymer in the oil when it is used as the oily gelling agent was investigated. Specifically, the oily gels shown in the following Table 7, in which an oily gelling agent was blended, were produced by the above-described production method, and they were evaluated by the above-described evaluation methods (1) to (3). Cetyl 2-ethylhexanoate was used as oil. The results are shown in Table 7 (the blending quantity is shown in % by mass).

SA 50/HEAA 50 is a copolymer consisting of stearyl acrylate vs N-(2-hydroxyethyl)acrylamide=50:50 (mole ratio). BEA 60/HEAA 40 is a copolymer consisting of behenyl acrylate vs N-(2-hydroxyethyl)acrylamide=60:40 (mole ratio).

According to Table 7, if the blending quantity of an oily gelling agent is too small, gelling property is poor, and if the blending quantity of an oily gelling agent is too large, the compatibility with oil is poor.

Accordingly, when the copolymer of the present invention is used as an oily gelling agent, the blending quantity of the oily gelling agent is preferably 2% by mass or higher in the composition, and more preferably 3% by mass or higher. The blending quantity of the oily gelling agent is preferably 10% by mass or less in the composition, and more preferably 8% by mass or less.

Next, the present inventors investigated the kinds of oils when the copolymer of the present invention is used as an oily gelling agent. Specifically, the oily gels shown in the following Table 8, in which an oily gelling agent was blended, were produced by the above-described production method, and they were evaluated by the above-described evaluation methods (1) and (2). The results are shown in Table 8 (the blending quantity is shown in % by mass).

TABLE 7

| Test example | 6-1 | 6-2 | 6-3 | 1-1 | 6-4 | 6-5 |
|---|---|---|---|---|---|---|
| SA 50/HEAA 50 | 1 | 2 | 3 | 5 | 8 | 10 |
| Cetyl 2-ethylhexanoate | 99 | 98 | 97 | 95 | 92 | 90 |
| Evaluation (1): Compatibility with oil | A | A | A | A | A | B |
| Evaluation (2): Gelling capability | C | C | A | A | A | A |
| Evaluation (3): Transparency | translucence | translucence | translucence | — | transparence | translucence |

| Test example | 6-6 | 6-7 | 6-8 | I-2 | 6-9 |
|---|---|---|---|---|---|
| BEA 60/HEAA 40 | 1 | 2 | 3 | 5 | 10 |
| Cetyl 2-ethylhexanoate | 99 | 98 | 97 | 95 | 90 |
| Evaluation (1): Compatibility with oil | A | A | A | A | B |
| Evaluation (2): Gelling capability | C | A | A | A | A |
| Evaluation (3): Transparency | translucence | translucence | translucence | translucence | translucence |

TABLE 8

| | Test example | 7-1 | 7-2 | 7-3 | 1-2 | 7-4 | 7-5 | 7-6 | 7-7 | 7-8 |
|---|---|---|---|---|---|---|---|---|---|---|
| | BEA 60/HEAA 40 | 5 | 5 | 5 | 5 | 5 | 5 | 5 | 5 | 5 |
| Hydrocarbon oil | Liquid paraffin | 95 | — | — | — | — | — | — | — | — |
| | Tetraisobutane | — | 95 | — | — | — | — | — | — | — |
| | Hydrogenated polydecene | — | — | 95 | — | — | — | — | — | — |
| Ester oil | Cetyl 2-ethylhexanoate | — | — | — | 95 | — | — | — | — | — |
| | Triethylhexanoin | — | — | — | — | 95 | — | — | — | — |
| Alcohol | Isostearyl alcohol | — | — | — | — | — | 95 | — | — | — |
| Silicone oil | Methylphenylpolysiloxane | — | — | — | — | — | — | 95 | — | — |
| | Dimethylpolysiloxane | — | — | — | — | — | — | — | 95 | — |
| | Cyclomethicone | — | — | — | — | — | — | — | — | 95 |
| Evaluation (1): Compatibility with oil | | A | A | A | A | A | A | A | C | C |
| Evaluation (2): Gelling property | | A | A | A | A | A | A | C | C | C |

According to Table 8, even when another ester oil, hydrocarbon oil, or alcohol is used as the oil instead of cetyl 2-ethylhexanoate, an oily gel could be obtained.

However, when silicone oil was used, an oily gel could not be obtained.

Accordingly, when the copolymer of the present invention is used as an oily gelling agent, hydrocarbon oil, ester oil, or alcohol is preferably contained as oil. In addition, silicone oil is not preferably contained as oil.

Next, water-in-oil type emulsion cosmetics wherein the oily gelled composition of the present invention, produced with the copolymer obtained by the above-described production method, were investigated. That is, the water-in-oil emulsion cosmetic shown in the following Table 9 were produced by the below-described production method, and they were evaluated by the above-described evaluation methods (4) and (5). The results are shown in Table 9.

BEA 60/GLM 40 is a copolymer consisting of behenyl acrylate vs glyceryl methacrylate=60:40 (mole ratio).

In Table 9, the one with the emulsion particle size of 15 µm or smaller was evaluated as A (acceptable) in the overall evaluation, and the one with the emulsion particle size of larger than 15 µm was evaluated as N/A (not acceptable) in the overall evaluation.

(Production Method)
After (1) to (5) were dissolved at 90° C., it was cooled with ice to 25° C., and an oily gelled composition was obtained. Subsequently, (6) was blended and mixed with a dispersion mixer (4000 rpm), and a water-in-oil type emulsion cosmetic was obtained.

TABLE 9

| Test example | 8-1 | 8-2 | 8-3 |
|---|---|---|---|
| (1) Cetyl 2-ethylhexanoate | 45 | 45 | 45 |
| (2) Liquid paraffin | 40 | 40 | 40 |
| (3) Dextrin palmitate | 5 | — | — |
| (4) BEA 60/HEAA 40 | — | 5 | — |
| (5) BEA 60/GLM 40 | — | — | 5 |
| (6) Ion-exchanged water | 10 | 10 | 10 |
| Evaluation (4): Viscosity (mPa · s) | 5300 | 10200 | 12900 |
| Evaluation (5): Emulsion particle size (µm) | ~75 | ~10 | ~12.5 |
| Overall evaluation | N/A | A | A |

According to Table 9, in the water-in-oil type emulsion cosmetic, in which the copolymer of the present invention was blended, a cosmetic with smaller emulsion particle sizes could be produced than in the cosmetic in which an oily gelled composition, containing the publicly known oily gelling agent dextrin palmitate, was blended.

In the following, formulation examples of oil-based cosmetics or water-in-oil type emulsion cosmetics, in which an oily gelled composition obtained by using the copolymer of the present invention is blended, are listed. The invention is not limited to the below formulation examples.

Formulation Example 1: Lip Gloss Composition

| Blending components | % by mass |
|---|---|
| (1) Diisostearyl malate | 39.9 |
| (2) BEA 60/HEAA 40 | 6.0 |
| (3) Hydrogenated lecithin | 0.1 |
| (4) Castor oil | 5.0 |
| (5) Liquid paraffin | 5.0 |
| (6) Heavy liquid isoparaffin | 40.0 |
| (7) 4-tert-butyl-4'-methoxydibenzoylmethane | 0.5 |
| (8) Calcium stearate | 0.5 |
| (9) Titanium oxide-covered synthesis gold mica | 1.0 |
| (10) Titanium oxide-covered glass powder | 1.0 |
| (11) Dipropylene glycol | 1.0 |

<Production Method>
1: Components (1) to (3) were dissolved at 95° C. and mixed.
2: Components (4) to (11) were dissolved at 85° C. and mixed.
3: 2 was gradually added to 1 and mixed with stirring.

The viscosity of the obtained lip gloss composition was 85,100 mPa·s (30° C.) and the stability was excellent.

Formulation Example 2: Lip Gloss Composition

| Blending components | % by mass |
|---|---|
| (1) Diisostearyl malate | 39.9 |
| (2) BEA 60/GLM 40 | 6.0 |
| (3) Hydrogenated lecithin | 0.1 |
| (4) Castor oil | 5.0 |
| (5) Liquid paraffin | 5.0 |
| (6) Heavy liquid isoparaffin | 40.0 |
| (7) 4-tert-butyl-4'-methoxydibenzoylmethane | 0.5 |
| (8) Calcium stearate | 0.5 |
| (9) Titanium oxide-covered synthesis gold mica | 1.0 |
| (10) Titanium oxide-covered glass powder | 1.0 |
| (11) Dipropylene glycol | 1.0 |

<Production Method>
1: Components (1) to (3) were dissolved at 95° C. and mixed.
2: Components (4) to (11) were dissolved at 85° C. and mixed.
3: 2 was gradually added to 1 and mixed with stirring.

The viscosity of the obtained lip gloss composition was 69,200 mPa·s (30° C.) and the stability was excellent.

Formulation Example 3: Pre-Mascara Composition

| Blending components | % by mass |
|---|---|
| (1) Light isoparaffin | 41.46 |
| (2) Microcrystalline wax | 20.00 |
| (3) Macademianut oil | 0.01 |
| (4) Sunflower oil | 0.01 |
| (5) Isostearic acid | 2.50 |
| (6) Glyceryl tri-2-ethylhexanoate | 2.00 |
| (7) dl-alpha-tocopherol acetate | 0.02 |
| (8) BEA 60/GLM 40 | 10.00 |
| (9) Decamethylcyclopentasiloxane | 8.00 |
| (10) Trimethylsiloxysilicate | 10.00 |
| (11) Titanium oxide-covered mica | 3.00 |
| (12) Nylon powder | 3.00 |

<Production Method>
1: Components (1) to (8) were dissolved at 95° C. and mixed.
2: Components (9) to (12) were mixed at 85° C. and dispersed.
3: 2 was gradually added to 1 and mixed with stirring.

The hardness of the obtained pre-mascara composition was 32 (30° C.) and the stability was excellent.

Formulation Example 4: Cream Composition

| Blending components | % by mass |
|---|---|
| (1) Hydrogenated polydecene | 60.000 |
| (2) Vaseline | 1.000 |
| (3) Isostearic acid | 0.100 |
| (4) Methylsiloxane reticulated polymer | 1.000 |
| (5) BEA 60/HEAA 40 | 6.000 |
| (6) Purified water | 15.437 |
| (7) Trisodium ethylenediaminetetraacetic acid | 0.100 |
| (8) Citric acid | 0.020 |
| (9) Sodium citrate | 0.080 |
| (10) Sodium pyrosulfite | 0.003 |
| (11) Sodium metaphosphate | 0.010 |
| (12) Arbutin | 3.000 |
| (13) Tranexamic acid | 1.000 |
| (14) Concentrated glycerin | 3.000 |
| (15) Dipropylene glycol | 3.000 |
| (16) Polyethylene glycol 1000 | 1.000 |
| (17) Ethanol | 5.000 |
| (18) Methyl paraben | 0.150 |
| (19) Sodium carboxymethylcellulose | 0.100 |

<Production Method>
1: Components (1) to (5) were mixed at 95° C. and dispersed.
2: Components (6) to (19) were mixed at 70° C. and dispersed.
3: 2 was gradually added to 1 and mixed with stirring.

The viscosity of the obtained W/O cream composition was 27,000 mPa·s (30° C.) and the stability was excellent.

What is claimed is:

1. A copolymer derived from a mixture consisting of a hydrophobic monomer unit having a general formula (1)

$$\begin{array}{c} \text{(1)} \\ \underset{OR^1}{\overset{O}{\underset{\|}{C}}}\!\!-\!\!\underset{R^2}{\overset{}{C}}\!\!=\!\!CH_2 \end{array}$$

wherein, $R^1$ is at least one alkyl group selected from the group consisting of straight chained and branched alkyl group, having 16 to 22 carbon atoms; and $R^2$ is selected from the group consisting of a hydrogen atom and a methyl;
and a hydrophilic monomer unit having a general formula (2)

$$\begin{array}{c} \text{(2)} \\ \underset{OR^3}{\overset{O}{\underset{\|}{C}}}\!\!-\!\!\underset{R^4}{\overset{}{C}}\!\!=\!\!CH_2 \end{array}$$

wherein $R^3$ is selected from the group consisting of glyceryl group, and polypropylene glycol group illustrated as $-(C_3H_6O)_nH$, wherein n is an integer of 2 to 10, $R^4$ is hydrogen or methyl;
and wherein the mole ratio of hydrophobic monomer (1) to hydrophilic monomer (2) ranges from 4:6 to 7:3.

2. The copolymer according to claim 1, wherein: said hydrophobic monomer having the general formula (1) is selected from the group consisting of cetyl (meth)acrylate, stearyl (meth)acrylate, and behenyl (meth)acrylate.

3. The copolymer according to claim 1, wherein: said hydrophilic monomer having the general formula (2) is selected from the group consisting of glyceryl methacrylate and PPG-6 acrylate.

4. The copolymer according to claim 1, wherein: said hydrophilic monomer having the general formula (2) is glyceryl methacrylate.

5. An oily gelling agent, comprising the copolymer according to claim 1.

6. An oily gelled composition comprising the oily gelling agent according to claim 5.

7. An oily cosmetic comprising the oily gelled composition according to claim 6.

8. A water-in-oil cosmetic comprising the oily gelled composition according to claim 6.

* * * * *